United States Patent [19]

Archibald

[11] 4,169,210

[45] Sep. 25, 1979

[54] OXIDATION OF DIETHYLBENZENES

[75] Inventor: William E. Archibald, Marietta, Ga.

[73] Assignee: Cosden Technology, Inc., Big Spring, Tex.

[21] Appl. No.: 496,644

[22] Filed: Aug. 12, 1974

[51] Int. Cl.$^2$ .......................................... C07C 179/02
[52] U.S. Cl. ................................................... 568/572
[58] Field of Search ...................... 260/610 B, 610 A; 568/572

[56] References Cited

U.S. PATENT DOCUMENTS

| | | | |
|---|---|---|---|
| 2,535,344 | 12/1950 | Bishop et al. | 260/610 B |
| 2,621,213 | 12/1952 | Joris | 260/610 B |
| 2,632,774 | 3/1953 | Conner et al. | 260/610 B |
| 2,633,476 | 3/1953 | Seubold | 260/610 B |
| 2,661,375 | 12/1953 | Conner | 260/601 |
| 2,796,439 | 6/1957 | Berneis | 260/610 B |
| 2,813,907 | 11/1957 | Vlugter | 260/610 B |

*Primary Examiner*—Werren B. Lone
*Attorney, Agent, or Firm*—Schwartz, Jeffery, Schwaab, Mack, Blumenthal & Koch

[57] ABSTRACT

A process for the oxidation of diethylbenzene comprising contacting an unpurified diethylbenzene feedstock with from about 0.01% to about 5.0% by weight of an alkaline earth metal oxide and concurrently and/or in a separate subsequent step contacting the diethylbenzene feedstock with a molecular oxygen-containing gas at a temperature between about 100° C. and 170° C. This process enables oxidation of diethylbenzenes to diethylbenzene hydroperoxide with a high degree of selectivity without the necessity of prior purification of the diethylbenzene feedstock, for example, by distillation or absorption techniques.

9 Claims, No Drawings

OXIDATION OF DIETHYLBENZENES

BACKGROUND OF THE INVENTION

The present invention relates to a process for oxidizing diethylbenzenes, and more particularly, it relates to a process for oxidizing diethylbenzenes with a molecular oxygen-containing gas without previously removing impurities from the diethylbenzene feedstock.

In view of the greatly increased demand for styrene in the past few years, there has resulted a concomitant increase in the availability of diethylbenzenes. It is already known to oxidize these diethylbenzenes to produce diethylbenzene hydroperoxide, which is useful in its own right as a free radical initiator and the like and, more importantly, is useful as an intermediate for the production of other compounds such as ethylphenols which find valuable utility in the preparation of additives for lubricating oils and as stabilizers for rubber, synthetic resins, oils, etc. In addition, the decrease in the supply of cresols has resulted in an increasing demand for substitutes such as ethylphenols.

The oxidation of diethylbenzenes to produce diethylbenzene hydroperoxide has been carried out by passing a molecular oxygen-containing gas through a diethylbenzene feedstock at a temperature generally between about 100° and 170° C. and at a pressure less than about 10 atmospheres, and generally at about atmospheric pressure. It has been observed in carrying out such a reaction that the selectivity in hydroperoxide is very poor if the diethylbenzene being treated is not of high purity. In particular, it has been found that the diethylbenzene must be free from the heavies and the colorbodies which generally are present in conventional diethylbenzene feedstocks, especially acids and arylvinyl compounds. Accordingly, it has been found necessary to purify the diethylbenzene feedstock in every instance before the same is subjected to oxidizing conditions in order to maintain an acceptable degree of selectivity for the hydroperoxide. This purification has in the past been carried out by passing the diethylbenzene feedstock through a pre-distillation step, followed preferably by an absorption step with silica gel or the like, prior to contacting the feedstock with the molecular oxygen-containing gas.

SUMMARY OF THE INVENTION

It is accordingly an object of the present invention to provide an improved process for the oxidation of diethylbenzenes to diethylbenzene hydroperoxide.

A further object of the present invention is to provide a process for the oxidation of diethylbenzenes which proceeds with good efficiency and evidences a consistently high selectivity for the hydroperoxide.

Yet another object of the present invention is the provision of a process for the oxidation of diethylbenzenes to diethylbenzene hydroperoxide which may be carried out with high selectivity to the hydroperoxide without the necessity of pretreating the diethylbenzene feedstock to remove conventional impurities.

In accomplishing the foregoing objects, there is provided in accordance with the present invention a process for the oxidation of diethylbenzene which comprises contacting an unpurified diethylbenzene feedstock with from about 0.01 to 5.0% by weight, and preferably from about 0.05 to 1.0% by weight, of an alkaline earth metal oxide, and concurrently and/or subsequently contacting the feedstock with a molecular oxygen-containing gas at a temperature between about 100° to 170° C., and preferably between about 130° and 150° C., to produce diethylbenzene hydroperoxide with a high degree of selectivity. Advantageously, the alkaline earth metal oxide is in a finely divided form, and the diethylbenzene feedstock may either be pre-treated by contact with the oxide before contacting the feedstock with the molecular oxygen-containing gas or the feedstock may be contacted with the oxide and the oxygen-containing gas at the same time. Alternatively, a combination of pre-treatment and concurrent treatment may be employed. The oxidation reaction may optionally be carried out in the presence of from about 0.01 to 0.5% by weight, based on the diethylbenzene, of an initiator selected from the group consisting of peroxy compounds and diazo compounds, with the preferred initiators being perbenzoates, tertiarybutylperoxide, diethylbenzene hydroperoxides and azobiscyclohexanenitrile.

Other objects, features and advantages of the present invention will become apparent from the detailed description of the invention which follows:

DETAILED DESCRIPTION OF THE INVENTION

The starting material for the process of the present invention is a diethylbenzene feed and may consist of a mixture of isomers. Such a mixed diethylbenzene feed is readily available from most alkylation processes used for the alkylation of benzene with ethylene to produce ethylbenzene. The mixed isomer feedstock may be oxidized as such to produce a mixture of diethylbenzene hydroperoxides, or alternatively, the different isomers of diethylbenzene may be first separated from one another before conducting the oxidation reaction. Thus, the meta-diethylbenzene may be separated from the ortho- and para-isomers by distillation and subsequently converted to meta-diethylbenzene hydroperoxide. The ortho-, para-mixture remaining after the initial distillation step may then be subjected to oxidation in accordance with the process of the present invention and the resulting ortho- and para-oxidation products can be separated. In a particularly useful embodiment of the present invention, the feed consists of meta-diethylbenzene in order to produce meta-substituted end products, such as meta-ethylphenol.

Commercially available diethylbenzene feedstocks contain a certain percentage of impurities which have been recognized to adversely affect the liquid phase oxidation of diethylbenzene by means of an oxygen-containing gas. For example, such feedstocks typically contain between about 0.1 and 5.0% by weight of heavy boiling constituents (the so-called "heavies") such as higher alkylbenzenes and the like, as well as from trace amounts to 2.0% by weight of the so-called "colorbodies" which consist primarily of acids, arylvinyl compounds, etc. These impurities have been recognized to have an adverse effect upon the rate of reaction and the degree of selectivity achieved when diethylbenzenes are oxidized with a molecular oxygen-containing gas. It was necessary, therefore, to in every instance subject the diethylbenzene feedstock to a preliminary treatment step wherein the various detrimental impurities were removed. Typically, this pre-treatment consists of a preliminary overhead distillation step, and in many cases, is accompanied by a subsequent absorption step wherein the distilled feedstock is further contacted with silica gel or the like in order to remove trace acid impurities. Failure to purify the diethylbenzene feedstock in this manner results in a very poor rate of the subsequent oxidation reaction, and sometimes spontaneous cessation of the reaction, as well as poor selectivity for the desired hydroperoxide product.

Often, diethylbenzene which has been treated in the foregoing manner becomes contaminated again during storage, probably as a result of autooxidation taking place. The resulting impurities, which are believed to be aromatic acids, are present only in very small amounts, e.g., measured in ppm; however, even these small amounts detrimentally affect the subsequent oxidation reaction.

In accordance with the present invention, it has been discovered that the preliminary purification treatment of the diethylbenzene feedstock may be completely eliminated and/or contaminated once-purified feed may be readily further purified without in any manner affecting the rate of reaction or selectivity for hydroperoxides if the feedstock is contacted with a small percentage of an alkaline earth metal oxide, preferably prior to and/or concurrently with the oxidation reaction. In conducting the process according to the present invention, the diethylbenzene feedstock may be first contacted with the oxide in a simple, but independent processing step prior to bringing the feedstock into contact with the oxygen-containing gas to effect the oxidation reaction. Alternatively, the feedstock may first be contacted with the oxide at the time the oxidation reaction is begun by passing the oxygen-containing gas through the diethylbenzene feedstock. Either of these modes of operation produces the advantageous results according to the present invention; however, in another embodiment of the invention, a combination of both procedures is employed. Thus, the feedstock is first contacted with alkaline earth metal oxide in a separate pre-processing step, and subsequently thereto, the thus-treated feedstock is conducted to a second vessel wherein the oxidation reaction takes place with the concurrent addition of further alkaline earth metal oxide. In this embodiment, the initial alkaline earth metal oxide-contacting step may be carried out by merely permitting the diethylbenzene feedstock to flow through a bed of finely divided oxide powder before the feedstock enters the oxidation reaction chamber, with additional oxide then being introduced into the feedstock as it enters the oxidation reaction chamber and the admission of oxygen-containing gas is initiated.

The amount of alkaline earth metal oxide with which the diethylbenzene feedstock is contacted in order to achieve the beneficial results according to the present invention ranges from about 0.01 to about 5% by weight based upon the feedstock. Preferably, this amount of magnesium oxide ranges between about 0.05 and about 1% by weight; however, in the preferred embodiment of the invention wherein the feedstock is twice contacted with the alkaline earth metal oxide, the amount employed at each individual contacting step typically ranges from about 0.05 to 0.5% by weight and preferably falls within the range of about 0.05 to 0.1% by weight.

In the embodiment of the invention according to which the alkaline earth metal oxide is contacted with the diethylbenzene feedstock in the oxidation vessel, the oxide is simply added to the feedstock in the stated amounts. On the other hand, when the feedstock is pre-treated with the oxide, the amount of alkaline earth metal oxide in the contacting device is determined by applying the above-defined relationship based upon the total volume of feedstock to be passed through the contacting device. Relatively smaller amounts within the above ranges are usually required with direct addition to the feedstock.

The alkaline earth metal oxide is preferably contacted with the diethylbenzene feedstock in a powdered or other relatively finely divided form, although the exact shape and size of the individual particles plays no significant role in the present invention. Thus, the individual particles may be as small as about $1\mu$ and as large as about $500\mu$, although in the usual instance, the particle size will range between about $10\mu$ and $100\mu$ in the embodiment where the oxide is added directly to the feedstock. Where pre-treatment is accomplished, the particle size of the alkaline earth metal oxide is preferably somewhat larger, for example, above about $50\mu$ and even up to ½ inch or even 1 inch.

In carrying out the oxidation reaction in accordance with the present invention, the diethylbenzene feedstock is contacted with a molecular oxygen-containing gas at a temperature which may vary from about 100° to 170° C. The oxidation rate of diethylbenzene typically increases as the reaction temperature is increased, and in order to minimize equipment sizes, it is desirable to carry out the reaction at the higher temperatures. However, the rates of formation of undesirable oxygenated by-products are also increased at higher temperatures, and consequently, the reaction temperature of the present process is generally maintained between about 130° and 150° C., and more particularly, between about 140° and 145° C. In a preferred embodiment of the invention, the oxidation is carried out by starting the reaction at about 150° C. and then progressively decreasing the temperature down to about 140° C. The period of reaction may be as short as ½ hour or as long as 3 hours, although the oxidation reaction is typically and practically carried out for a period ranging between about 1 and 2 hours.

The oxidizing agent may be air, oxygen or other molecular oxygen-containing gas. Air has the advantage of a lower cost, but oxygen permits higher throughput per unit reactor volume. The ultimate choice of the molecular oxygen-containing gas depends, however, primarily upon economic conditions. The oxidation reaction is carried out by passing the molecular oxygen-containing gas into liquid diethylbenzene under conditions insuring a rapid and intimate contact between the two phases, for example, by employing a bubble-column or a reactor with a stirring device. In order to avoid an excessive formation of undesirable by-products, especially acid compounds which catalyze the decomposition of the product hydroperoxide, it is desirable to use the oxygen-containing gas in controlled amounts. A large excess of the gas is detrimental with respect to the selectivity of the process, and for this reason, the amount of oxygen in the vent gas is preferably kept below about 20% and more preferably below about 10%.

The oxidation reaction may be carried out at atmospheric pressure or at somewhat higher pressures. However, it has been found that pressures higher than about 10 atmospheres do not result in improved yields, and therefore, pressures lower than 10 atmospheres are generally employed.

The oxidation reaction proceeds according to a chain mechanism with free radicals as chain propagators. Accordingly, it may be desirable to initiate this mechanism by means other than thermal self-initiation. Suitable initiators include peroxy compounds, such as perbenzoates, tertiary-butyl peroxide, diethylbenzene hydroperoxide, and diazo compounds, such as azobiscyclohexanenitrile, which are soluble in the feed and which decompose at the reaction temperature to produce initiating radicals. An initiator is employed advantageously not only to reduce the induction period at the beginning of the reaction, but also to maintain a high rate of initiation, i.e., a high rate of oxidation, throughout the course of the reaction. The amount of initiator employed depends largely on its efficiency at the chosen temperature, but it generally does not exceed about 5% by weight based on the feed material. At temperatures higher than about 140° C., the thermal self-initiation is sufficiently rapid that the addition of an initiator is not necessary.

As stated hereinabove, the selectivity of the present process for the production of diethylbenzene monohydroperoxide depends to a great extent upon the purity of the feedstock material. In addition, this selectivity also depends to some extent upon the reaction conditions as set forth above, upon the presence of initiators in the reaction system and also upon the degree of conversion. The effect of degree of conversion is due partly to the detrimental effect of the by-products obtained by the thermal decomposition of the hydroperoxides which progressively accumulate. This effect also results from the fact that the diethylbenzene monohydroperoxide is oxidized to an increasing extent to other hydroperoxide compounds, and mainly to bishydroperoxide and ethyl acetophenone hydroperoxide. Therefore, it is preferable to limit the diethylbenzene conversion, and it has been found that the most useful conversions lie between about 5 and 30%, and more particularly, between about 10 and 25%.

As stated above, the diethylbenzene hydroperoxides obtained according to the process of the present invention are advantageously further processed to form other useful products, for example, by the decomposition thereof in the presence of a strong acid to form ethylphenol.

The following examples are presented to more fully illustrate the present invention, it being understood that they are to be considered as merely illustrative and under no circumstances limitative.

COMPARATIVE EXAMPLE A 402 grams of meta-diethylbenzene is taken directly from a barrel and exhibits a slightly yellow color. The composition of this feedstock is approximately as follows: 99.1% metadiethylbenzene, 0.1% ortho-diethylbenzene, 0.6% para-diethylbenzene, 0.6% butylbenzenes, 0.1% ethylbenzene, and normal oxidative impurities. The feedstock is subjected to a distillation procedure and is stripped overhead, whereupon it is then treated with silica gel to yield a colorless, nearly pure meta-diethylbenzene starting product. The feedstock is then placed in a stainless steel reactor equipped with a stirring device, a cooling system and a condenser. Air is bubbled into the liquid with agitation at a rate of approximately 60 liters per hour. The reaction mass is then heated up to 150° C. at which temperature oxygen uptake begins rapidly. After about 20 minutes, the oxygen percentage in the vent gas is depressed to about 9 to 10% and remains at this value throughout the course of the reaction. The temperature is progressively decreased as the diethylbenzene conversion increases in such a way that a temperature of 140° C. is reached at a diethylbenzene conversion value of about 22%, as determined by oxygen absorption measurements. This conversion is obtained after about 150 minutes, and the reaction mixture is then rapidly cooled to about 30° to 40° C. and collected.

The rate of oxidation is calculated to be about 9% per hour and the final selectivity to diethylbenzene monohydroperoxide is found to be 89%.

COMPARATIVE EXAMPLE B

The procedure of Example A is repeated except that the pre-treatment steps of distillation and contact with silica gel are eliminated and the unpurified meta-diethylbenzene feedstock is added directly to the reaction vessel. Under these conditions, the reaction proceeds at a substantially slower rate with the rate of oxidation being about 5% per hour. A conversion of only about 16 mol % is achieved, since the oxidation reaction ceased spontaneously after about 180 minutes. The final selectivity to the monohydroperoxide is only about 66.5%.

EXAMPLE 1

The procedure of Example B is repeated except that 0.3 grams of magnesium oxide (finely divided powder of about 50μ average particle size) is added to the reactor together with the diethylbenzene feedstock. This amount corresponds to 0.07 weight % magnesium oxide based on the total feedstock. The rate of oxidation in accordance with this procedure is found to be 10.3% per hour and the final selectivity to the monohydroperoxide is 85.4%.

EXAMPLE 2

100,000 lb. of m-diethylbenzene feedstock as in Example A is passed through a tower containing 100 lb. of MgO having an average particle size of about ¼ inch. This corresponds to about 0.1% of the MgO based upon the total feedstock. The feedstock is subjected to oxidation with air at a temperature of 140° C. 150 minutes residence time produces a conversion value of 24% with an 85% selectivity for diethylbenzene hydroperoxide. The MgO bed did not diminish in its effectiveness to remove impurities from the M-DEB over the course of the run.

EXAMPLE 3

10,000 lbs. of m-diethylbenzene feedstock of Example A is slurried with 100 lbs. of MgO having an average particle size of about 100μ, the slurry is filtered to remove the MgO therefrom and is then sent to an oxidation reactor. The reactor is operated under conditions as in Example 2 and equivalent improved results relative to the untreated feedstock are observed.

Thus, there has been provided in accordance with the present invention an improved process for the liquid phase oxidation of diethylbenzenes to the corresponding diethylbenzene monohydroperoxides. In accordance with this process, a high rate of oxidation and a high final selectivity for the monohydroperoxide are achieved without the necessity of conducting an additional pre-oxidation step to purify commercially available diethylbenzene feedstock used for the oxidation reaction. This process provides an excellent back-up system for a conventional diethylbenzene oxidation process in the eventuality that an impure diethylbenzene feedstock is unexpectedly encountered and no distillation capacity is readily available to purify the feedstock.

It is apparent that various modifications, additions and substitutions may become readily apparent to persons of ordinary skill in the art on the basis of the foregoing description, without departing from the spirit of the present invention. Therefore, it is to be understood that the scope of protection is to be determined solely by the claims appended hereto.

What is claimed is:

1. A process for the oxidation of diethylbenzene which comprises contacting an unpurified diethylbenzene feedstock with from about 0.01 to 5% by weight of an agent consisting essentially of an alkaline earth metal oxide in finely divided form having a particle size between about 50μ and 1 inch by passing said feedstock through a first reaction vessel containing a bed of said alkaline earth metal oxide, in a pretreatment stage conveying said pre-treated feedstock to a second reaction vessel and contacting said feedstock with a molecular oxygen-containing gas at a temperature between about 100° C. and 170° C. in said second vessel whereby said diethylbenzenes are oxidized to diethylbenzene monohydroperoxide with high selectivity without the necessity of prior purification of the diethylbenzene feedstock to remove therefrom impurities normally detrimental to said oxidation reaction.

2. The process as defined by claim 1, wherein the diethylbenzene feedstock is contacted with from about 0.05 to 1% by weight of said alkaline earth metal oxide.

3. The process as defined by claim 1, wherein the oxidation is carried out at a temperature between about 130° C. and 150° C.

4. The process as defined by claim 3, wherein the oxidation is carried out by starting the reaction at about 150° C. and then progressively decreasing the reaction temperature to about 140° C.

5. The process as defined by claim 1, wherein the alkaline earth metal oxide is magnesium oxide.

6. The process as defined by claim 1, wherein the oxidation is carried out in the presence of from about 0 to 5% by weight based on the diethylbenzene of a free radical generating initiator selected from the group consisting of peroxy compounds and diazo compounds.

7. The process as defined by claim 6, wherein the initiator is selected from the group consisting of perbenzoates, tertiary-butyl peroxide, diethylbenzene hydroperoxide and azobiscyclohexanenitrile.

8. The process as defined by claim 1, wherein the amount of oxygen in the vent gas issuing from the oxidation is maintained below about 20% by volume.

9. The process as defined by claim 1, wherein said process is carried out in a continuous manner.

* * * * *